(12) United States Patent
Sarr et al.

(10) Patent No.: US 7,444,876 B2
(45) Date of Patent: *Nov. 4, 2008

(54) RAPID PROTOTYPE INTEGRATED LINEAR ULTRASONIC TRANSDUCER INSPECTION APPARATUS, SYSTEMS, AND METHODS

(75) Inventors: Dennis P. Sarr, Kent, WA (US); Hien T. Bui, Auburn, WA (US)

(73) Assignee: The Boeing Company, Chicago, IL (US)

( * ) Notice: Subject to any disclaimer, the term of this patent is extended or adjusted under 35 U.S.C. 154(b) by 378 days.

This patent is subject to a terminal disclaimer.

(21) Appl. No.: 11/213,652

(22) Filed: Aug. 26, 2005

(65) Prior Publication Data

US 2007/0044563 A1    Mar. 1, 2007

(51) Int. Cl.
  *G01N 29/04* (2006.01)
(52) U.S. Cl. .............................. 73/618; 73/620; 73/635; 73/641
(58) Field of Classification Search .................. 73/618, 73/620, 635, 866.5, 633, 640, 641, 644
See application file for complete search history.

(56) References Cited

U.S. PATENT DOCUMENTS

| | | |
|---|---|---|
| 3,575,042 A | 4/1971 | Lovelace et al. |
| 3,789,350 A | 1/1974 | Rolle |
| 3,958,451 A | 5/1976 | Richardson |
| 4,010,636 A | 3/1977 | Clark et al. |
| 4,103,234 A | 7/1978 | Frazier, Jr. |
| 4,117,733 A | 10/1978 | Gugel |
| 4,160,386 A | 7/1979 | Jackson et al. |
| 4,167,880 A | 9/1979 | George |
| 4,173,897 A | 11/1979 | Fostermann et al. |
| 4,173,898 A | 11/1979 | Fostermann et al. |
| 4,229,796 A | 10/1980 | Garrett |
| 4,311,052 A | 1/1982 | Jeffras et al. |
| 4,327,588 A | 5/1982 | North |
| 4,365,514 A | 12/1982 | Ho |
| 4,368,644 A | 1/1983 | Wentzell et al. |
| 4,399,703 A | 8/1983 | Matzuk |
| 4,466,286 A | 8/1984 | Berbeé et al. |
| 4,470,304 A | 9/1984 | Nusbickel, Jr. et al. |
| 4,474,064 A | 10/1984 | Naruse et al. |
| 4,559,825 A | 12/1985 | Martens |

(Continued)

FOREIGN PATENT DOCUMENTS

DE    28 31 395 A1    1/1980

(Continued)

OTHER PUBLICATIONS

*Abstract & Claim 1 only.

(Continued)

*Primary Examiner*—Hezron E. Williams
*Assistant Examiner*—Jacques M. Saint-Surin
(74) *Attorney, Agent, or Firm*—Alston & Bird LLP

(57) ABSTRACT

Apparatus, systems, and methods for inspecting a structure are provided which use a sensor holder constructed from rapid prototyping, such as stereolithography, and which is configured to support one or more linear inspection sensors. Rapid prototype integrated linear ultrasonic transducer inspection apparatus, systems, and methods provide fast and efficient methods of constructing custom inspection devices.

21 Claims, 5 Drawing Sheets

U.S. PATENT DOCUMENTS

| | | | |
|---|---|---|---|
| 4,612,808 A | 9/1986 | McKirdy et al. | |
| 4,752,895 A | 6/1988 | Sarr | |
| 4,755,953 A | 7/1988 | Geithman et al. | |
| 4,803,638 A | 2/1989 | Nottingham et al. | |
| 4,807,476 A | 2/1989 | Cook et al. | |
| 4,848,159 A | 7/1989 | Kennedy et al. | |
| 4,912,411 A | 3/1990 | Allison et al. | |
| 5,007,291 A * | 4/1991 | Walters et al. | 73/640 |
| 5,047,771 A | 9/1991 | Engeler et al. | |
| 5,062,301 A | 11/1991 | Aleshin et al. | |
| 5,241,135 A | 8/1993 | Fetzer | |
| 5,396,890 A | 3/1995 | Weng | |
| 5,417,218 A | 5/1995 | Spivey et al. | |
| 5,485,084 A | 1/1996 | Duncan et al. | |
| 5,535,628 A * | 7/1996 | Rutherford | 73/622 |
| 5,567,881 A * | 10/1996 | Myers | 73/629 |
| 5,593,633 A | 1/1997 | Dull et al. | |
| 5,621,414 A | 4/1997 | Nakagawa | |
| 5,698,787 A | 12/1997 | Parzuchowski et al. | |
| 5,786,535 A | 7/1998 | Takeuchi et al. | |
| 5,902,935 A | 5/1999 | Georgeson et al. | |
| 5,963,882 A | 10/1999 | Viertl et al. | |
| 5,986,549 A | 11/1999 | Teodorescu | |
| 6,057,927 A | 5/2000 | Levesque et al. | |
| 6,167,110 A | 12/2000 | Possin et al. | |
| 6,220,099 B1 | 4/2001 | Marti et al. | |
| 6,474,164 B1 | 11/2002 | Mucciardi et al. | |
| 6,484,583 B1 | 11/2002 | Chennell et al. | |
| 6,507,635 B2 | 1/2003 | Birdwell et al. | |
| 6,641,535 B2 * | 11/2003 | Buschke et al. | 600/437 |
| 6,658,939 B2 | 12/2003 | Georgeson et al. | |
| 6,711,235 B2 | 3/2004 | Galish et al. | |
| 6,722,202 B1 | 4/2004 | Kennedy et al. | |
| 6,725,721 B2 | 4/2004 | Venczel | |
| 6,748,791 B1 | 6/2004 | Georgeson et al. | |
| 6,772,635 B1 * | 8/2004 | Sale et al. | 73/622 |
| 6,829,959 B2 * | 12/2004 | Gifford et al. | 73/866.5 |
| 6,839,636 B1 | 1/2005 | Sunshine et al. | |
| 6,843,130 B2 | 1/2005 | Georgeson | |
| 6,843,312 B2 | 1/2005 | Burk et al. | |
| 6,848,312 B2 | 2/2005 | Georgeson | |
| 6,895,079 B2 | 5/2005 | Birdwell et al. | |
| 6,927,560 B2 | 8/2005 | Pedigo et al. | |
| 7,050,535 B2 | 5/2006 | Georgeson et al. | |
| 7,055,389 B2 | 6/2006 | Mueller | |
| 7,064,332 B2 * | 6/2006 | Favro et al. | 250/341.6 |
| 7,228,741 B2 | 6/2007 | Georgeson et al. | |
| 7,231,826 B2 | 6/2007 | Bossi et al. | |
| 7,240,556 B2 | 7/2007 | Georgeson et al. | |
| 7,249,512 B2 * | 7/2007 | Kennedy et al. | 73/618 |
| 7,253,908 B2 * | 8/2007 | Vaccaro et al. | 356/607 |
| 7,263,889 B2 * | 9/2007 | Kennedy et al. | 73/620 |
| 2004/0237653 A1 | 12/2004 | Graff et al. | |
| 2006/0243051 A1 * | 11/2006 | Bui et al. | 73/618 |
| 2007/0044563 A1 * | 3/2007 | Sarr et al. | 73/618 |
| 2007/0044564 A1 * | 3/2007 | Bui et al. | 73/618 |

FOREIGN PATENT DOCUMENTS

| | | |
|---|---|---|
| DE | 28 52 560 B1 | 1/1980 |
| DE | 198 26 759 C1 | 12/1999 |
| DE | 100 43 199 A1 | 9/2002 |
| EP | 1 193 491 A2 | 4/2002 |
| JP | 09 264877 A | 10/1997 |

OTHER PUBLICATIONS

U.S. Appl. No. 10/943,088, filed Sep. 16, 2004; Inventors: Georgeson, entitled *Magnetically Attracted Inspecting Apparatus and Method Using a Ball Bearing*.

U.S. Appl. No. 10/943,135, filed Sep. 16, 2004, Inventors: Georgeson, entitled *Magnetically Attracted Inspecting Apparatus and Method Using a Fluid Bearing*.

U.S. Appl. No. 11/041,499, filed Jan. 24, 2005, Inventors: Kennedy, entitled *Non-Destructive Stringer Inspection Apparatus and Method*.

Stereolithography Made Easy, *What is Rapid Prototyping?*, available at http://www.stereolithography.com/rapidprototyping.php, May 23, 2005, 11 pages.

GE Inspection Technologies: Array Transducers, *Ultrasonic Array Probes*, available at http://www.geinspectiontechnologies.com/products/Ultrasonics/IndustrialProbes/aplparrays.html, dated Mar. 24, 2005, 2 pages.

*Linear Arrays*, available at http://www.ob-ultrasound.net/lineararrays.html, dated Mar. 24, 2005, 2 pages.

* cited by examiner

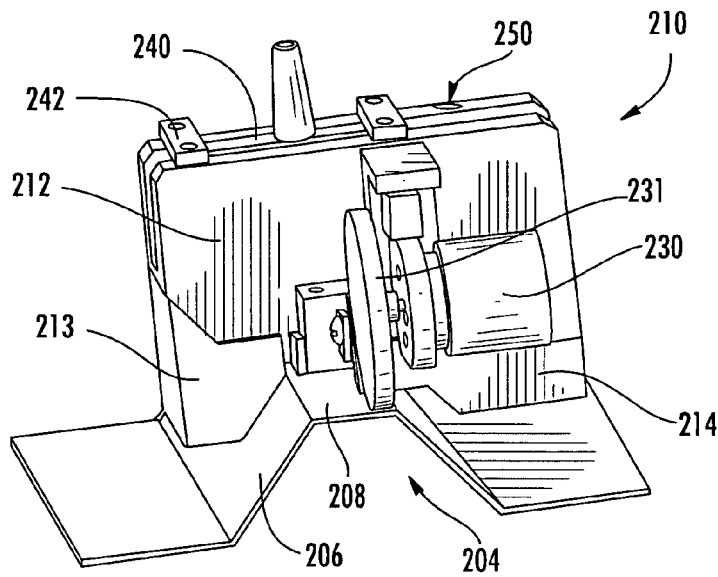
FIG. 6
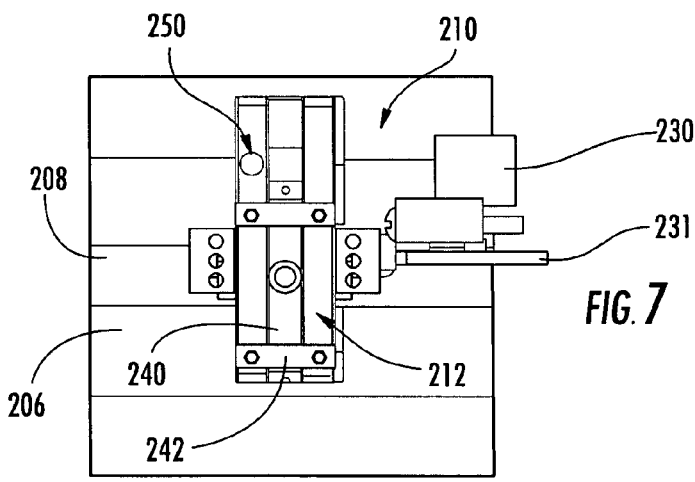
FIG. 7
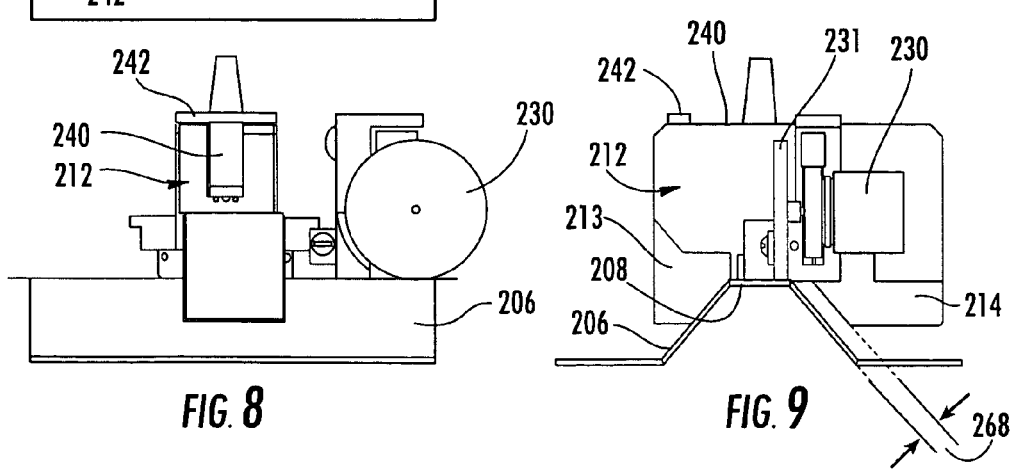
FIG. 8
FIG. 9

RAPID PROTOTYPE INTEGRATED LINEAR ULTRASONIC TRANSDUCER INSPECTION APPARATUS, SYSTEMS, AND METHODS

CROSS-REFERENCE TO RELATED APPLICATIONS

The contents of U.S. Pat. No. 6,722,202; application Ser. No. 10/943,088, entitled "Magnetically Attracted Inspecting Apparatus and Method Using a Ball Bearing," filed Sep. 16, 2004; application Ser. No. 10/943,135, entitled "Magnetically Attracted Inspecting Apparatus and Method Using a Fluid Bearing," filed Sep. 16, 2004; and application Ser. No. 11/041,499, entitled "Non-Destructive Stringer Inspection Apparatus and Method," filed Jan. 24, 2005, are incorporated herein by reference in their entireties.

FIELD OF THE INVENTION

The present invention relates generally to an apparatus and method for inspecting a structure and, more particularly, embodiments of the present invention relate to apparatus, systems, and methods for non-destructive inspection of a structure using rapid prototype integrated linear ultrasonic transducers.

BACKGROUND

Non-destructive inspection (NDI) of structures involves thoroughly examining a structure without harming the structure or requiring significant disassembly of the structure. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or defects (flaws) in the structure. Inspection may be performed during manufacturing of a structure or after the completed structure has been put into service, including field testing, to validate the integrity and fitness of the structure during manufacturing and ongoing and future use while in-service.

Among the structures that are routinely non-destructively tested are composite structures, such as composite sandwich structures and other adhesively bonded panels and assemblies and structures with contoured surfaces, such as hat stringers or hat stiffeners made from carbon fiber reinforced and graphite epoxy (Gr/Ep) materials and co-cured or co-bonded hat stringers. These composite structures, and a shift toward lightweight composite and bonded materials such as using graphite materials, dictate that devices and processes are available to ensure structural integrity, production quality, and life-cycle support for safe and reliable use. As such, it is frequently desirable to inspect structures to identify any defects, such as cracks, discontinuities, voids, or porosity, which could adversely affect the performance of the structure. For example, typical defects in composite sandwich structures, generally made of one or more layers of lightweight honeycomb or foam core material with composite or metal skins bonded to each side of the core, include disbonds which occur at the interfaces between the core and the skin or between the core and a buried septum.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, and/or crack detection in the structure. Resonance, pulse echo, or impedance sensors may be used to provide indications of voids or porosity, such as in adhesive bondlines of the structure. High resolution inspection of an aircraft structure is commonly performed using semi-automated ultrasonic testing (UT) to provide a plan view image of the part or structure under inspection. While solid laminates and some composite structures are commonly inspected using one-sided pulse echo ultrasonic (PEU) testing, composite sandwich structures are commonly inspected using through-transmission ultrasonic (TTU) testing for high resolution inspection. In pulse echo ultrasonic (PEU) testing, ultrasonic sensors, such as ultrasonic transducers, are positioned adjacent to or near one surface of the structure to be inspected. For example, the PEU transducer transmits an ultrasonic signal into the structure under inspection and receives the reflection of the ultrasonic signal from the structure. In through-transmission ultrasonic inspection, ultrasonic sensors such as transducers, or a transducer and a receiver sensor, are positioned facing the other but contacting opposite sides of the structure. An ultrasonic signal is transmitted by at least one transducer, propagated through the structure, and received by the other transducer. Data acquired by sensors is typically processed and then presented to a user via a display as a graph of amplitude of the received signal. A data acquisition board and data handling software may be used for collection and display of inspection data, such as displaying the data on a computer monitor as an image representation of the structure under inspection, such as a hat stringer, supplemented with corresponding color and/or graphical data of the inspection to permit examination by a qualified inspector.

Non-destructive ultrasonic testing often involves coupling an ultrasonic signal from a transducer or transducer array to the surface of the structure under inspection, such as bubbling water between an inspection device and the structure. While solid laminates may be inspected using one-sided pulse echo ultrasonic (PEU) testing and bondline thickness may be measured using one-sided pulse echo ultrasonic testing, composite sandwich structures typically require through-transmission ultrasonic (TTU) testing for high resolution inspection. In through-transmission ultrasonic inspection, ultrasonic sensors such as transducers, or a transducer and a receiver sensor, are positioned facing the other but contacting opposite sides of the structure to be inspected such as opposite surfaces of a composite material. An ultrasonic signal is transmitted by at least one of the transducers, propagated through the structure, and received by the other transducer. Data acquired by sensors, such as PEU and TTU transducers, is typically processed by a processing element, and the processed data may be presented to a user via a display.

Non-destructive inspection may be performed manually by technicians who move an appropriate sensor over the structure. Manual scanning generally consists of a trained technician holding a sensor and moving the sensor along the structure to ensure the sensor is capable of testing all desired portions of the structure. In many situations, the technician must repeatedly move the sensor side-to-side in one direction while simultaneously indexing the sensor in another direction. For a technician standing beside a structure, the technician may repeatedly move the sensor right and left, and back again, while indexing the sensor between each pass. In addition, because the sensors typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician in interpreting the displayed data.

Semi-automated inspection systems have been developed to overcome some of the shortcomings with manual inspection techniques. For example, the Mobile Automated Scanner (MAUS®) system is a mobile scanning system that generally employs a fixed frame and one or more automated scanning heads typically adapted for ultrasonic inspection. A MAUS system may be used with pulse-echo, shear wave, and through-transmission sensors. The fixed frame may be attached to a surface of a structure to be inspected by vacuum suction cups, magnets, or like affixation methods. Smaller MAUS systems may be portable units manually moved over the surface of a structure by a technician. However, for through-transmission ultrasonic inspection, a semi-automated inspection system requires access to both sides of a structure which, at least in some circumstances, will be problematic, if not impossible, particularly for semi-automated systems that use a fixed frame for control of automated scan heads.

Automated inspection systems have also been developed as an alternative to manual and semi-automated inspection techniques. For single sided inspection methods, such as pulse echo ultrasonic inspection, a single-arm robotic device, such as an R-2000iA™ series six-axis robot from FANUC Robotics of Rochester Hills, Mich., or an IRB 6600 robot from ABB Ltd. of Zurich, Switzerland, may be used to position and move a pulse echo ultrasonic inspection device. For through transmission inspection, a device such as the Automated Ultrasonic Scanning System (AUSS®) system may be used. The AUSS system has two robotically controlled probe arms that can be positioned proximate the opposed surfaces of the structure undergoing inspection with one probe arm moving an ultrasonic transmitter along one surface of the structure, and the other probe arm correspondingly moving an ultrasonic receiver along the opposed surface of the structure. Conventional automated scanning systems, such as the AUSS-X system, therefore require access to both sides of a structure for through transmission inspection which, at least in some circumstances, will be problematic, if not impossible, particularly for very large or small structures. To maintain the transmitter and receiver in proper alignment and spacing with one another and with the structure undergoing inspection, the AUSS-X system has a complex positioning system that provides motion control in ten axes. The AUSS system can also perform pulse echo inspections, and simultaneous dual frequency inspections.

To increase the rate at which the inspection of a structure is conducted, a scanning system may include arrays of inspection sensors, i.e., arrays of transmitters and/or detectors. As such, the inspection of the structure can proceed more rapidly and efficiently, thereby reducing the costs associated with the inspection. Similarly, a scanning system may include a linear ultrasonic transducer (also referred to as a linear array transducer, in comparison to an unordered or matrix array). However, typically each structure and inspection application requires a corresponding transducer or transducer array designed to provide transducer alignment (position and orientation with respect to the surface(s) of the structure) and scan coverage for the structure. Conventionally, special inspection devices are constructed for scanning different structures and different sizes and configurations of structures. Designing an inspection device using one or more linear inspection sensors for scanning a particular structure requires ensuring proper alignment of the inspection sensors with respect to the surface(s) of the structure and ensuring scan coverage of the structure. For example, consideration must be taken for flat and curved surfaces as well as features of the structure, including radius features such as convex edges and concave corners. Constructing specialized inspection devices for each inspection application conventionally has required significant time and financial and human resources to design and build these specialized inspection devices. Also, conventionally, each specialized inspection device is designed for and capable of only inspecting one structure, and typically cannot adjust for different sizes of the structure or different inspection applications that use different linear inspection sensor sizes.

Accordingly, a need exists for improved non-destructive inspection apparatus, systems, and methods for inspecting a structure.

SUMMARY OF THE INVENTION

Improved apparatus, systems, and methods for inspecting a structure, such as inspecting structures with multiple sides and/or difficult to inspect features using one or more linear inspection sensors, are provided which use a sensor holder constructed from rapid prototyping, such as stereolithography, and which is configured to support a linear inspection sensor aligned for inspection of a structure, particularly structures such as hat stringers. Embodiments of methods of the present invention provide fast and efficient methods of constructing custom inspection devices for inspecting structures with linear inspection sensors (also referred to as linear array inspection sensors), rather than an array of individual inspection sensors.

According to another aspect of the present invention, to facilitate coupling of ultrasonic signals between linear inspection sensors of apparatus and systems of embodiments of the present invention, such as linear pulse echo ultrasonic sensors, a couplant may be disposed between the linear inspection sensors and a respective surface of the structure under inspection. An apparatus of an embodiment of an inspection device according to the present invention may advantageously include a fluid manifold capable of feeding a fluid couplant between a linear inspection sensor and a surface of the structure to couple ultrasonic signals of the linear inspection sensor to the structure.

According to another aspect of the present invention, a method for constructing custom inspection devices for inspecting structures with one or more linear inspection sensors is provided, such as inspection devices configured to support a linear inspection sensor aligned for inspection of a structure.

These and other characteristics, as well as additional details, of the present invention are further described in the Detailed Description with reference to these and other embodiments.

BRIEF DESCRIPTION OF THE DRAWING(S)

Having thus described the invention in general terms, reference will now be made to the accompanying drawings, which are not necessarily drawn to scale, and wherein:

FIG. 6 is a perspective view of an inspection device of another embodiment of the present invention for inspecting a hat stringer;

FIG. 7 is a top plan view of a schematic diagram of the inspection device of FIG. 6;

FIG. 8 is a side elevation view of a schematic diagram of the inspection device of FIG. 6;

FIG. 9 is a front elevation view of a schematic diagram of the inspection device of FIG. 6;

DETAILED DESCRIPTION

Figure 1:
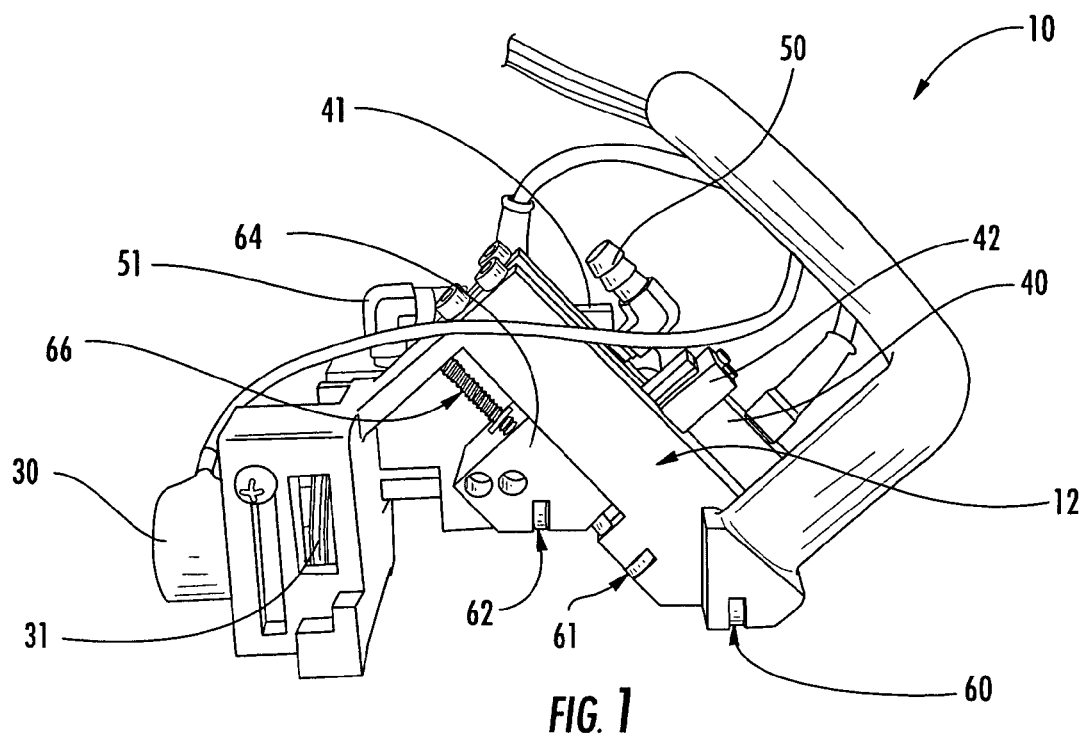
FIG. 1 is a perspective view of an inspection device of an embodiment of the present invention for inspecting a hat stringer.

The present invention will be described more fully with reference to the accompanying drawings. Some, but not all, embodiments of the invention are shown. The invention may be embodied in many different forms and should not be construed as limited to the described embodiments. Like numbers and variables refer to like elements and parameters throughout the drawings.

While embodiments of the present invention are described herein with reference to pulse echo ultrasonic (PEU) non-destructive inspection and typically would be used with linear pulse echo ultrasonic non-destructive inspection sensors, embodiments of the present invention are not limited to one-sided inspection methods, but may be used for other inspection methods, including, without limitation, through transmission ultrasonic inspection. For example, inspection of hat stringers and other structures with complex configurations may be more easily inspected using an embodiment of the present invention employing a one sided inspection method such as pulse echo ultrasonic inspection; however, magnetically coupled inspection probes may use embodiments of the present invention for through transmission ultrasonic inspection.

Embodiments of rapid prototype integrated linear ultrasonic transducer inspection apparatus, systems, and methods of the present invention are described herein with respect to inspection of hat stringers, especially composite hat stringers for an aircraft fuselage. However, the apparatus, systems, and methods may also be used for structures other than hat stringers and similar applications which require non-destructive inspection, including without limitation other composite structures with difficult-to-inspect geometric configurations and/or remote locations. Embodiments of apparatus, systems, and methods of the present invention may be used for manual hand scanning by a technician or using a semi-automatic or automatic robotic motion control system, possibly also using magnetic coupling such as described with reference to the magnetically coupled probes in co-pending applications Ser. Nos. 10/943,088; 10/943,135; and 11/041,499. One advantage of embodiments of the present invention is that rapid prototyping permits creation of inspection devices with custom shapes for custom inspection applications according to the corresponding shapes and features of the structure to be inspected, such as the multi-sided surfaces of a hat stringer. Accordingly, embodiments of apparatus and systems according to the invention may be designed and constructed to accommodate variations of structure shapes, sizes, and other characteristics, such as different hat stringer design shapes, sizes, and part thickness changes. A rapid prototype structure of an inspection apparatus for supporting a linear ultrasonic transducer is referred to herein as a sensor holder.

An embodiment of an apparatus according to the invention may be designed to have a surface-side (the portion of the apparatus proximate and/or riding on a structure under inspection) of the sensor holder corresponding to the shape of at least a portion of the surface of the structure, where at least a portion of the structure includes a curved feature such as a corner, edge, groove, or non-planar surface such as a convex or concave surface. For example, if the structure to be inspected has a concave shape, the surface-side of the apparatus may be designed to have a convex shape that fits the concave shape of the structure. Similarly, if the structure to be inspected is a hat stringer, the apparatus may be designed to correspond to the shapes, sizes, and corner angles of the hat stringer. For example, an apparatus designed to inspect a side web of a hat stringer, may be designed (shaped, sized, etc.) to conform to the structure, to support a linear transducer aligned to provide inspection coverage of the side web of the hat stringer. For example, the apparatus may include one or more concave or convex corners to respectively match with one or more of the corners between the top cap and the side webs of the hat stringer and one or more of the corners between the side webs of the hat stringer and where the hat stringer attaches to the superstructure. The inspection device of an embodiment of the present invention shown in FIGS. 1-5 includes two concave corners to match the two corners between the top cap and the side webs of the hat stringer and one convex corner to match a corner between the side webs of the hat stringer and where the hat stringer attaches to the superstructure. The inspection device of an embodiment of the present invention shown in FIGS. 6-9 includes two concave corners and two convex corners. The inspection device of an embodiment of the present invention shown in FIGS. 10-12 includes one concave corner and two convex corners.

The design and use of a sensor holder according to the present invention permits full coverage inspection of structures using linear inspection sensors. A linear inspection sensor only inspects in one dimension, such as scanning a y-axis while the x-axis is at a fixed position. However, by using a sensor holder according to the present invention, full inspection coverage is possible. By scanning in a specific pattern, such as placing a linear inspection sensor across the width of a hat stringer and then passing the linear inspection sensor along the length of the hat stringer, full inspection coverage can be achieved.

Inspection devices, and particularly the sensor holders of inspection devices, of embodiments of the present invention are designed to correspond to the shape and size of structures to be inspected. For example, the inspection devices 10, 210, and 310 depicted in FIGS. 1-5, 6-9, and 10-12 are intended for inspection of web sides and top caps of hat stringers. For example, the sensor holders 12 and 212 of inspection devices 10 and 210 each are designed for traveling over at least a portion of a hat stringer structure for inspecting the top cop and/or web side of the hat stringer. The sensor holder 312 of the inspection device 310 is configured for traveling over and inspecting either a web side or a top cap of a hat stringer. The inspection devices 10, 210, 310 each have concave corners and/or convex corners corresponding to the angles of the corners of the web side-top cap intersection of the hat stringer and/or the groove between the web side of the hat stringer and the structure skin. Similarly, the inspection devices 10, 210, 310 each are designed with a flat, surface-side portions designed for traveling over the web sides and/or cap top of a hat stringer. One commonality between the inspection devices 10, 210, 310 is that that each includes at least one orientation corner for riding along a corner, in a groove, or with respect to another fixed portion of a structure under inspection, thereby providing orientation between the hat stringer or other structure and the inspection device for a reference and to provide consistency for inspection operations.

Embodiments of the present invention may be constructed by rapid prototyping as a single part or in multiple parts which are assembled. For example, a single apparatus may be constructed with (i) rectangular sensor recesses for supporting linear inspection sensors, (ii) a handle for manual inspection operations and handling the inspection device, (iii) a structural holder for supporting an encoder, such as an optical shaft encoder, and (iv) a fluid manifold recess for providing fluid flow from a fluid inlet port to a region between a linear inspection sensor and a structure, thereby coupling ultrasonic signals of the linear inspection sensors to the structure. Alternatively, for example, individual pieces of an apparatus may be constructed that can be assembled. Inspection devices, and particularly sensor holders, of embodiments of the present invention may advantageously be fabricated by rapid prototyping (RP, also known as rapid manufacturing, solid freeform fabrication, computer automated manufacturing, and layered manufacturing). Rapid prototyping involves slicing an electronic design model into electronic layers which are physically built up to create the end product, such as stereolithography which constructs three-dimensional end products from liquid photosensitive polymers (e.g., liquid epoxy or acrylate resin) that solidify when exposed to ultraviolet light (e.g., low-power focused UV laser that traces out each layer). Stereolithography is further described in U.S. Pat. No. 4,575,330 to Hull, assigned to 3D Systems, Inc., of Valencia, Calif. Other types of rapid prototyping are also possible, such as laminated object manufacturing, selective laser sintering, fused deposition modeling, solid ground curing, and 3-D ink-jet printing. Rapid prototyping does not require tooling because the end product is produced directly from an electronic design model, typically a CAD model. Because rapid prototyping does not require tooling, it provides a relatively inexpensive and fast method of manufacturing a custom inspection device. Rapid prototyping is particularly advantageous for custom inspection devices because a CAD model can be created for the particular application corresponding to the structure to be inspected, and a corresponding inspection device can be created. Embodiments of the present invention can be created in relatively little time, for relatively low cost while still being designed specifically for a particular inspection application, even if the structure to be inspected has a unique shape or surface contour.

Figure 2:
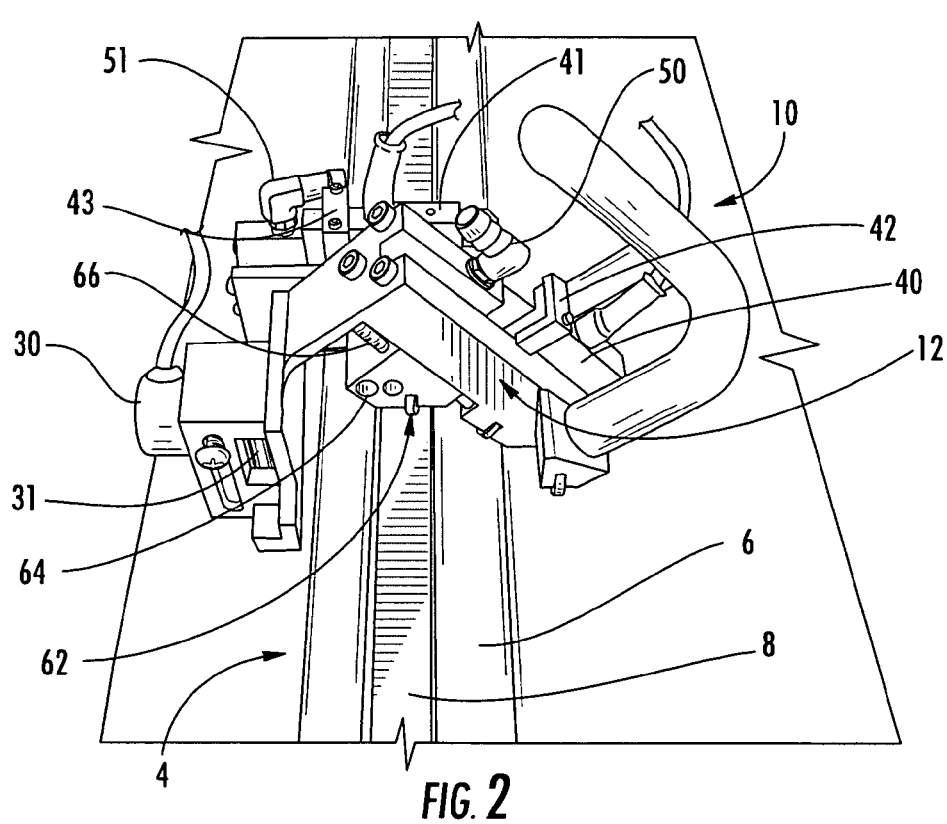
FIG. 2 is another view of the inspection device of FIG. 1.
Figure 3:
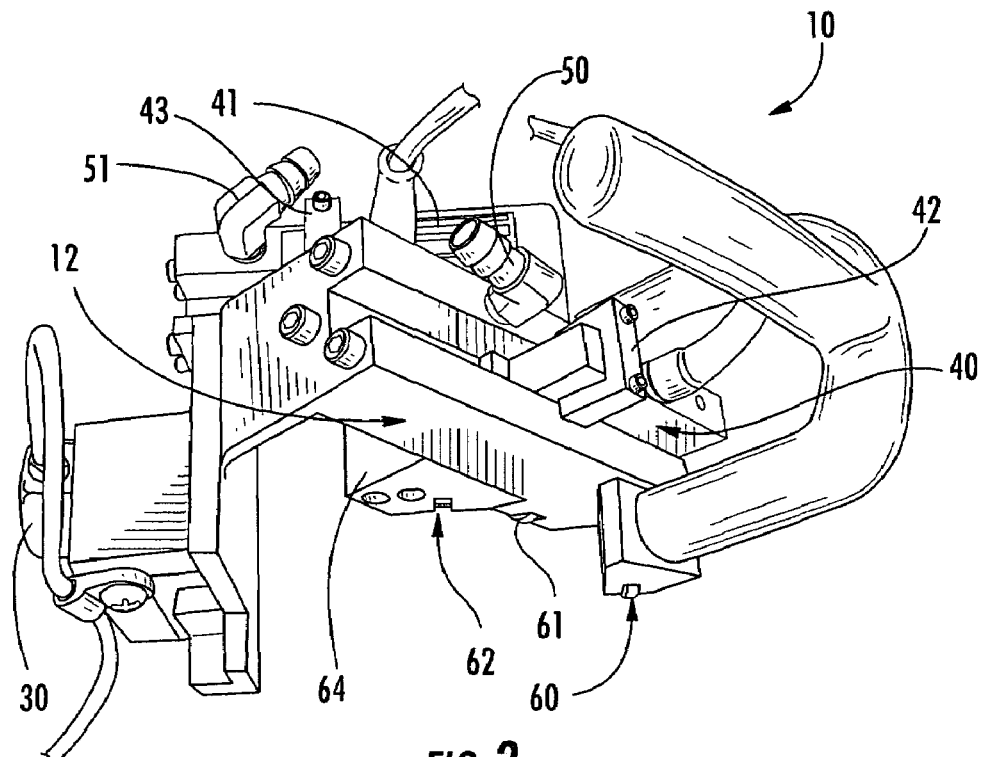
FIG. 3 is yet another view of the inspection device of FIG. 1.
Figure 4:
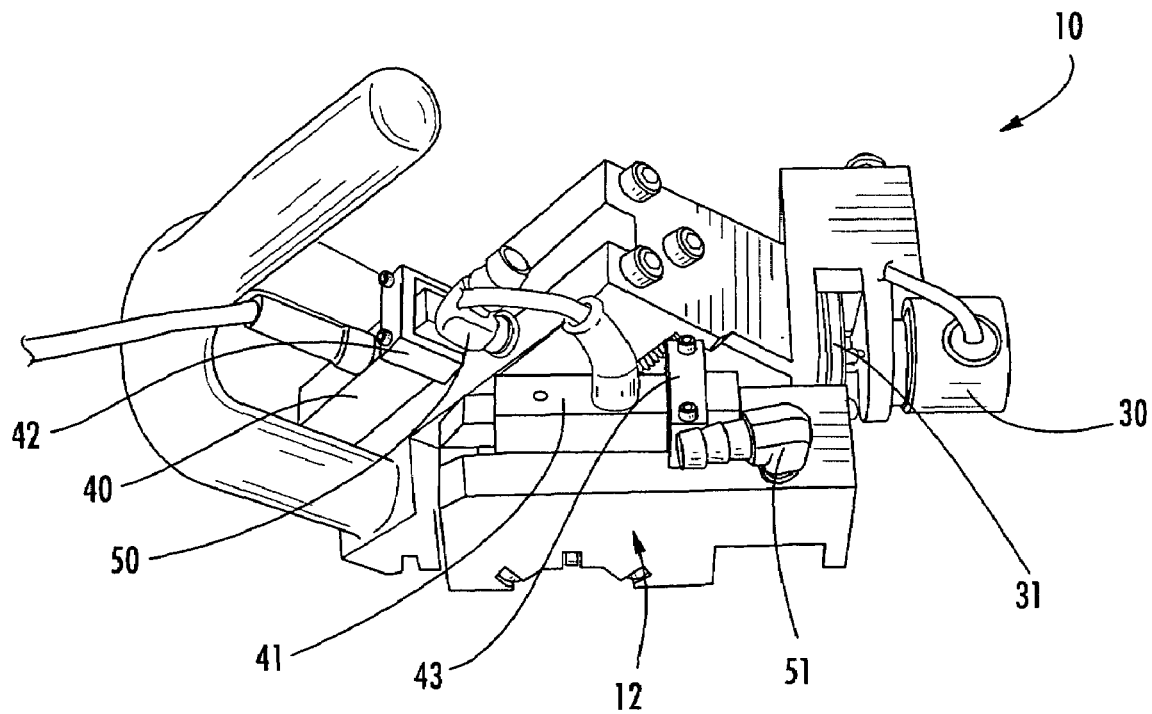
FIG. 4 is yet another view of the inspection device of FIG. 1.
Figure 5:
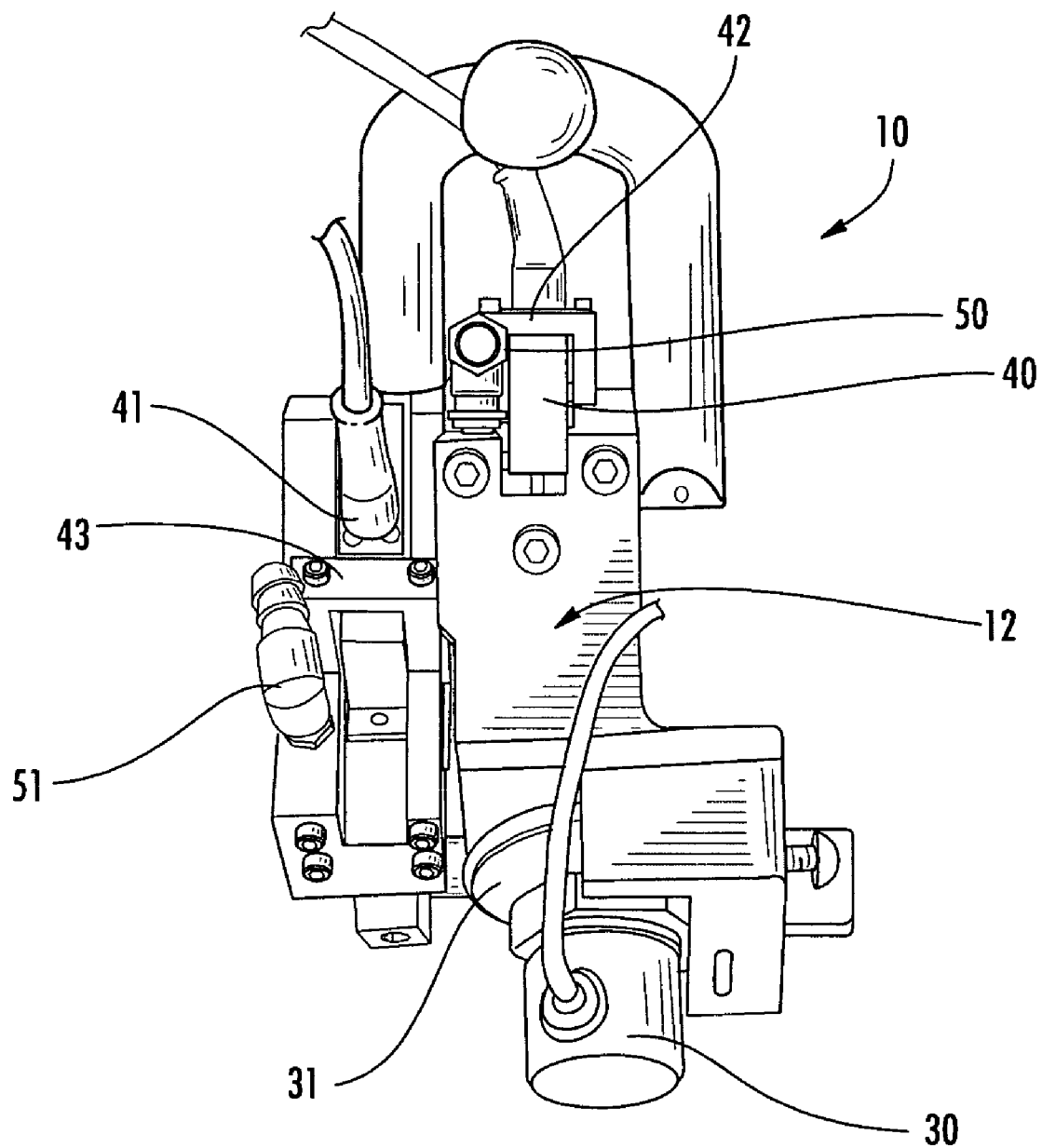
FIG. 5 is yet another view of the inspection device of FIG. 1.

FIGS. 1-5 show an inspection device 10 according to an embodiment of the present invention. FIG. 1 is a side perspective view of the inspection device 10; FIG. 3 is a top and side angled perspective view of the inspection device 10; FIG. 4 is a top and side angled perspective view of the inspection device 10 opposite the angle of FIG. 3; and FIG. 5 is a top perspective view of the inspection device 10. FIG. 2 shows an inspection device 10 placed on a hat stringer 4 as the inspection device 10 might be used for an inspection operation of a web side 6 and cap top 8 of the hat stringer 4.

The inspection device 10 includes two linear transducers 40, 41. The linear transducers 40, 41 are supported by the rapid prototyped sensor holder 12 of the inspection device 10 in such a manner that one linear transducer 40 is oriented to inspect the web side 6 of the hat stringer 4 and the other linear transducer 41 is oriented to inspect the top cap 8 of the hat stringer 4. The sensor holder 12 defines a rectangular recesses into which the linear transducers 40, 41 are secured, such as by u-shaped holders (transducer supports) 42, 43 that are screwed down to the sensor holder 12. A sensor holder may be configured to permit adjustment for inspection structures of different shapes and sizes. For example, the sensor holder 12 of FIGS. 1-5 includes an adjustable corner portion 64 which is positioned my adjusting the rotation of an alignment screw 66 that controls the movement of the adjustable corner portion 64 along the length of the alignment screw 66. Similarly, the u-shaped holders 42, 43 and rectangular recesses are configured to permit adjustment of the position of linear transducers 40, 41 and replacement of the linear transducers 40, 41 with linear transducers of different lengths, such as a longer linear transducer for inspecting a hat stringer with a wider web side portion or a wider top cap portion.

An inspection device may also include contact members, such as roller bearings 60, 61, 62 or skids, to extend outwardly from the face or surface of the sensor holder of the inspection device that faces respective surfaces of a structure under inspection. Various types of contact members can be used, such as roller bearings, ball bearings, fluid bearings, skids or the like. Skids may include a Teflon® material available from E.I. DuPont Nemours and Company of Wilmington, Del., on a surface of the skid for contact with the surface of the structure being inspected and to provide for translation thereacross. Skids may be beneficial to prevent damage or marring of a surface of a structure under test when initially placing an inspection device on a structure. Fluid bearings, such as water bearings and air bearings, may be used to maintain spacing and orientation of an inspection device with respect to a structure under inspection. Bearings, skids, and the like may be used to reduce the fiction between the inspection device and the surface of the structure under inspection, such as displace the probe from contacting the surface of the structure using hydraulic flotation or a hydrostatic bearing. Use of contact members may provide smooth translation of an inspection device over the surface of a structure to allow an inspection device to maintain an intended direction, maintain alignment of inspection sensors, and allow continuous scanning of a surface regardless of size, smoothness, or flatness of the surface, such as to permit easy rolling of the inspection device. Further, use of a skid or fluid bearing between the inspection device and the surface of the structure may prevent scratching of soft skins or denting of panels of the skins.

For ultrasonic inspection operations, a fluid, like water or air, can be fed through one or more supply lines through a fluid inlet port and into one or more recesses, such as defined channels or manifolds, a central cavity, or similar openings that permit the flow of fluid throughout the inspection device, within an inspection device to disperse the fluid between the inspection device, and particularly the inspection sensors supported thereby, and the structure, thereby coupling test signals between the inspection sensors and the structure. This process is known as fluid coupling. Generally an attempt is made to have the fluid flow smoothly between the inspection sensors and the structure without bubbles, cavitations, or turbulence that might detrimentally affect the signal to noise ratio of the ultrasonic inspection signals. The inspection device 10 includes fluid inlet ports 50, 51 to which fluid supply lines may be connected to deliver a fluid couplant to the inspection device 10. The fluid inlet ports 50, 51 are connected to internal fluid manifolds within the sensor holder 12 that are configured to pass a fluid couplant from the fluid inlet ports 50, 51 to the area between the linear transducers 40, 41 and the structure under inspection, such as the web side 6 and cap top 8 of the hat stringer 4.

Figure 10:
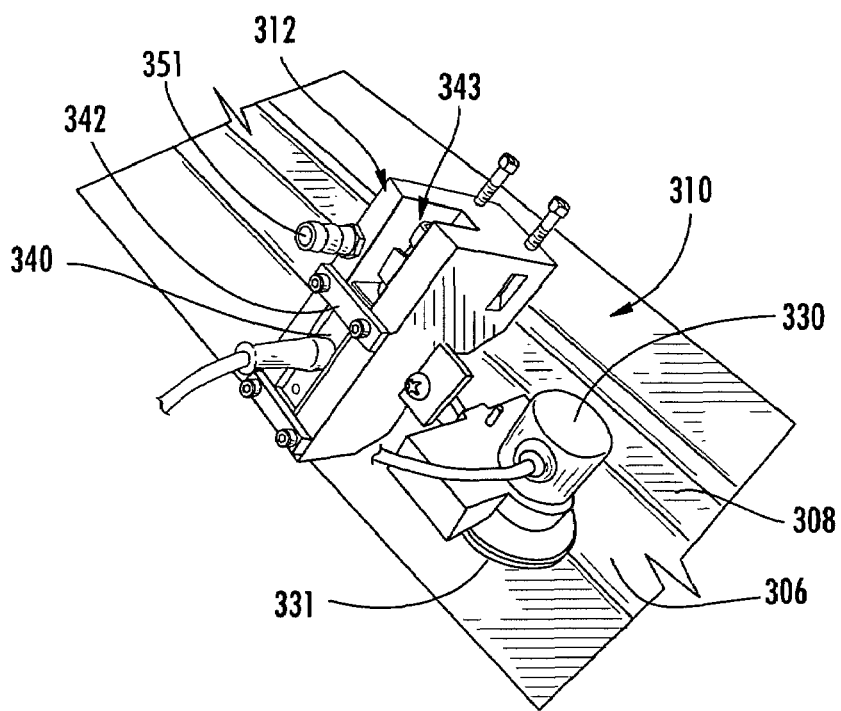
FIG. 10 is a perspective view of an inspection device of yet another embodiment of the present invention for inspecting a hat stringer.
Figure 11:
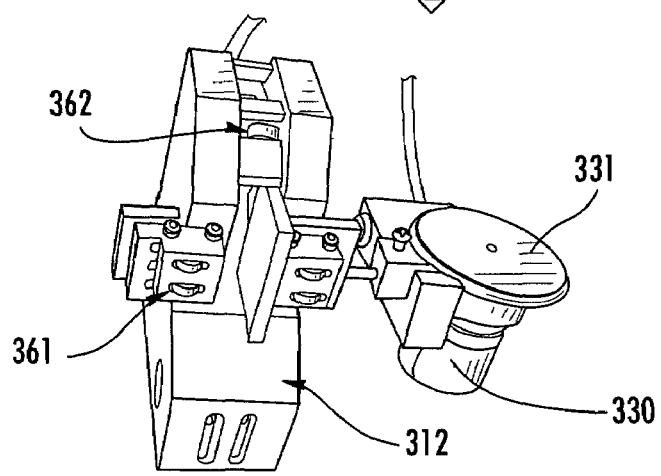
FIG. 11 is another view of the inspection device of FIG. 10.
Figure 12:
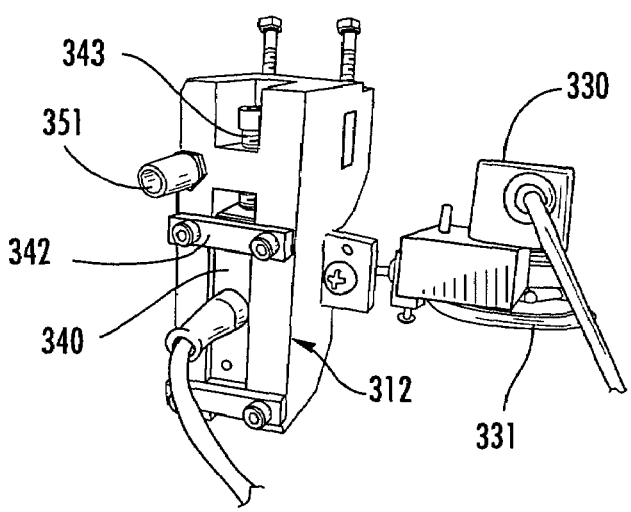
FIG. 12 is yet another view of the inspection device of FIG. 11.

The inspection device 10 also includes an optical shaft encoder (OSE) or linear encoder 30 with a wheel 31 for recording motion or position information of the inspection device 10 with respect to the hat stringer 4 being inspected. The optical shaft encoder 30 and wheel 31 are mounted to the inspection device to operate by traveling along the structure adjacent to a web side 6 of a hat stringer 4; however, alternative embodiments may use encoders which are oriented to operate at different locations, such as along a web side or top cap of a hat stringer as shown in the embodiment of FIGS. 10-12, and/or which are mounted in such a manner to permit adjustment as needed for inspection of different structures, such as hat stringers with different heights and/or sizes. Similarly to the use of a wheel attachment 31 for an optical shaft encoder 30, other embodiments of inspection devices in accordance with the present invention may be used with a drive motor or like automated drive mechanism to semi-automatically or automatically move an inspection device along a structure for inspection; alternatively, a magnetically coupled crawler or motion controlled robotic arm maybe use used to control movement of an inspection device along a structure for inspection.

FIGS. 6-9 show an inspection device 210 of another embodiment of the present invention. By comparison to the embodiment of FIGS. 1-5, the inspection device 210 of FIGS. 6-9 includes an optical shaft encoder 230 oriented with a wheel 231 that contacts and rides along the cap top 208 of the hat stringer 204. The inspection device 210 also differs from that of FIGS. 1-5, in that the sensor holder 212 is configured with segmented portions 213, 214 that may separate for inspecting hat stringers with wider cap tops as indicated by a separation 268 in FIG. 9. Alternatively, the segmented portions 213, 214 may be exchanged with different segmented portions for inspecting hat stringers with different angles between the cap top and web sides. The main portion of the sensor holder 212, the optical shaft encoder 230, and wheel 231 remain unchanged as they are oriented with respect to a cap top surface of a hat stinger, and a cap top of a hat stringer will remain constant regardless of the width, height, angles, etc. of the hat stringer. In like manner and orientation of the wheel 231 of the optical shaft encoder 230, a drive motor or like automated drive mechanism may be attached to the inspection device 210 to move the inspection device 210 along a hat stringer for semi-automatic or automatic inspection operations. Unlike the embodiment of FIGS. 1-5, the inspection device 210 of FIGS. 6-9 uses a flat transducer support 242. Various types of transducer supports may be used with other embodiments of inspection devices in accordance with the present invention, including, but not limited to, transducer supports which provide a removable and adjustable enclosure for the top opening of a recess, thereby capable of securing a linear transducer in a recess but permitting removal of the transducer support for extraction of the linear transducer from the recess.

FIGS. 10-12 show an inspection device 310 of yet another embodiment of the present invention. The inspection device 310 is a smaller and simpler version of an apparatus in accordance with the present invention than the inspection devices 10, 210 of FIGS. 1-5 and 6-9. The inspection device 310 is configured for and may be used for inspection of various sizes of web sides and cap tops of hat stringers. Similar to the inspection devices 10, 210 of FIGS. 1-5 and 6-9, the inspection device 310 includes a linear transducer 340, transducer support 342, fluid inlet port 351, and roller bearings 361, 362. The inspection device 310 also includes a transducer positioning screw 343 for pushing the linear transducer 340 to the end of the rectangular recess such that one end of the linear transducer 340 will be located at a known position corresponding to a reference position for inspection operations such that the one end of the linear transducer 340 and the reference position correspond and the linear transducer 340 scans a structure beginning at the reference position and continues along the length of the linear transducer 340.

As previously mentioned, embodiments of the present invention may be used in manual scanning operations, such as where an operator slides an inspection device along a structure, or may be used in semi-automated or automated scanning operations. Also, as previously mentioned, sensor holders of embodiments of the present invention may be made in various configurations to conform to equally varying configurations of structures to be scanned using linear transducers and/or be adjustable or have exchangeable portions to permit use of a sensor holder on more than one shaped or sized structure. Further, sensor holders and inspection devices of embodiments of the present invention may be used for inspection of multiple portions of a structure, such as the embodiment of FIGS. 10-12 that may be used for scanning a web side or a cap top of a hat stringer, and/or may be used with multiple linear transducers for simultaneous inspection of different portions of a structures, such as the embodiment of FIGS. 1-5 that may be used for inspection all or a portion of both a web side and a cap top of a hat stringer.

The invention should not be limited to the specific disclosed embodiments and modifications and other embodiments of the invention are intended to be included within the scope of the appended claims. Specific terms are used in a generic and descriptive sense only and not for purposes of limitation.

That which is claimed:

1. A non-destructive inspection apparatus for inspecting a structure, comprising:
   a sensor holder defining at least one recess for supporting and orienting at least one linear inspection sensor configured to inspect over a continuous first length in a first dimension without movement of the linear inspection sensor in the first dimension, wherein the first length substantially corresponds to the length of the linear inspection sensor, wherein the sensor holder is configured for traveling over at least a first portion of the structure, wherein the first portion of the structure comprises at least one curved structural feature.

2. The apparatus of claim 1, wherein the sensor holder is configured for inspecting and traveling over at least a portion of a hat stringer.

3. The apparatus of claim 1, wherein the sensor holder further defines a handle for manual inspection of a structure.

4. The apparatus of claim 1, wherein the recess is configured with an adjustable alignment screw capable of securing a linear inspection sensor along the length of the recess by pressing the linear inspection sensor against the opposite end of the recess from the alignment screw.

5. The apparatus of claim 4, wherein the sensor holder is further configured with an adjustable corner portion capable of being relocated to correspond with the position of the alignment screw such that the adjustable corner portion defines a position of a concave corner of the sensor holder corresponding to the position where one end of a linear inspection sensor is secured by the alignment screw against the opposite end of the recess from the alignment screw.

6. The apparatus of claim 5, wherein the sensor holder is further configured such that the alignment screw is capable of both adjusting the position of the adjustable corner portion and securing a linear inspection sensor along the length of the recess by pressing the corner portion against the linear inspection sensor.

7. The apparatus of claim 1, wherein the recess is configured with at least one removable and adjustable enclosure capable of securing a linear inspection sensor disposed in the recess by holding the linear inspection sensor into the recess.

8. The apparatus of claim 1, wherein the sensor holder is further configured to define a first recess for supporting and orienting a first linear inspection sensor at a first angle to the structure to permit a linear inspection sensor supported by the first recess to inspect a first portion of the structure and a second recess for supporting and orienting a second linear inspection sensor at a second angle to the structure to permit a linear inspection sensor supported by the second recess to inspect a second portion of the structure while the sensor holder travels over the first and second portions of the structure.

9. The apparatus of claim 1, further comprising at least one linear inspection sensor disposed in, supported by, and oriented by a recess defined by the sensor holder.

10. The apparatus of claim 1, further comprising a fluid manifold and a fluid inlet port connected to the fluid manifold, wherein the fluid inlet port is configured for injecting a fluid into the fluid manifold, and wherein the sensor holder is further configured for permitting the dispersion of fluid from the fluid manifold between the at least one recess and the structure.

11. The apparatus of claim 10, wherein the sensor holder is further configured to define the fluid manifold.

12. The apparatus of claim 10, further comprising at least one linear inspection sensor disposed in a recess defined by the sensor holder and wherein the fluid manifold is configured for permitting the dispersion of fluid from the fluid manifold between the linear inspection sensor and the structure.

13. The apparatus of claim 1, further comprising an encoder configured for measuring at least one of the following characteristics of the inspection apparatus with respect to the structure under inspection: position, speed, direction, and velocity.

14. The apparatus of claim 1, further comprising a motion device capable of moving the sensor holder over at least the first portion of the structure, wherein the motion device is configured for moving the sensor holder over the structure along an axis perpendicular to the end-to-end orientation of the at least one linear inspection sensor supported in the at least one recess such that any linear inspection sensors carried by the sensor holder move sideways over the structure for inspection of the at least first portion of the structure.

15. The apparatus of claim 14, wherein the motion device comprises a motor with an attached wheel.

16. A system for inspecting a structure comprising:
a sensor holder configured for traveling over at least a first portion of the structure under inspection, wherein the sensor holder defines at least one recess for supporting and orienting at least one linear inspection sensor disposed in the at least one recess, the linear inspection sensor configured to inspect over a continuous first length in a first dimension without movement of the linear inspection sensor in the first dimension, wherein the first length substantially corresponds to the length of the linear inspection sensor, and wherein the sensor holder is configured for traveling over at least the first portion of the structure under inspection, wherein the first portion of the structure comprises at least one curved structural feature; and
at least one linear inspection sensor disposed in the at least one recess and carried by the sensor holder for inspecting the structure as the sensor holder is moved over the structure.

17. The system of claim 16, further comprises a fluid manifold and a fluid inlet port connected to the fluid manifold, wherein the fluid inlet port is configured for injecting a fluid into the fluid manifold, wherein the sensor holder is further configured for permitting the disbursement of fluid from the fluid manifold to an area between at least one linear inspection sensor and a portion of the structure, and wherein the sensor holder defines the fluid manifold.

18. The system of claim 16, further comprising a motor carried by the sensor holder and configured to move the sensor holder over at least the first portion of the structure.

19. The system of claim 18, wherein the sensor holder is configured for inspecting hat stringers.

20. The system of claim 16, further comprising an encoder carried by the sensor holder and configured for measuring at least one of the following characteristics of the sensor holder with respect to the structure under inspection: position, speed, direction, and velocity.

21. The system of claim 16, wherein the sensor holder is further configured to define a handle for manual inspection of a structure.

* * * * *